US010890571B2

(12) United States Patent
Nakano

(10) Patent No.: US 10,890,571 B2
(45) Date of Patent: Jan. 12, 2021

(54) CONTROL APPARATUS AND GAS DETECTION METHOD

(71) Applicant: NGK Spark Plug Co., LTD., Nagoya (JP)

(72) Inventor: Yoshihiro Nakano, Komaki (JP)

(73) Assignee: NGK Spark Plug Co., LTD., Nagoya (JP)

( * ) Notice: Subject to any disclaimer, the term of this patent is extended or adjusted under 35 U.S.C. 154(b) by 97 days.

(21) Appl. No.: 16/204,685

(22) Filed: Nov. 29, 2018

(65) Prior Publication Data
US 2019/0187114 A1 Jun. 20, 2019

(30) Foreign Application Priority Data

Dec. 15, 2017 (JP) .................... 2017-240425

(51) Int. Cl.
| | | |
|---|---|---|
| G01N 27/26 | (2006.01) | |
| G01N 33/00 | (2006.01) | |
| G01N 27/416 | (2006.01) | |
| G01N 27/409 | (2006.01) | |
| F02D 41/00 | (2006.01) | |
| G01N 27/417 | (2006.01) | |

(52) U.S. Cl.
CPC ......... *G01N 33/0037* (2013.01); *F02D 41/00* (2013.01); *G01N 27/409* (2013.01); *G01N 27/416* (2013.01); *G01N 27/417* (2013.01)

(58) Field of Classification Search
CPC ......... F02D 41/1459; F02D 2041/1468; F01N 2900/1626; F01N 3/103; G01N 33/0037

USPC ......................................................... 73/23.32
See application file for complete search history.

(56) References Cited

U.S. PATENT DOCUMENTS

| | | | | |
|---|---|---|---|---|
| 7,231,290 | B2 * | 6/2007 | Steichen | F01N 3/0842 |
| | | | | 701/109 |
| 2003/0037538 | A1 * | 2/2003 | Rendahl | F01N 11/00 |
| | | | | 60/276 |

FOREIGN PATENT DOCUMENTS

JP 2011-47758 A 3/2011

* cited by examiner

*Primary Examiner* — Angelo Trivisonno
(74) *Attorney, Agent, or Firm* — Leason Ellis LLP

(57) ABSTRACT

A control apparatus mounted on a diesel vehicle including an oxidation catalyst, a selective reduction catalyst, and a gas sensor includes an activation determination section, a concentration computation section, and a deterioration determination section. The concentration computation section computes the concentration of flammable gas from a sensor output in a period during which the activation determination section determines that the oxidation catalyst is not in the activated state and computes the concentration of ammonia gas from the sensor output in a period during which the activation determination section determines that the oxidation catalyst is in the activated state. The deterioration determination section determines whether or not the oxidation catalyst has deteriorated, on the basis of the concentration of the flammable gas computed by the concentration computation section.

11 Claims, 7 Drawing Sheets

CONTROL APPARATUS AND GAS DETECTION METHOD

This application claims the benefit of Japanese Patent Application No. 2017-240425, filed Dec. 15, 2017, which is incorporated herein by reference in its entirety.

FIELD OF THE INVENTION

The present invention relates to a control apparatus mounted on a diesel vehicle which includes an oxidation catalyst capable of oxidizing flammable gas contained in exhaust gas, a selective reduction catalyst capable of reducing nitrogen oxides contained in the exhaust gas by using ammonia gas, and a gas sensor configured to be sensitive to both the ammonia gas and the flammable gas, and to a gas detection method for detecting a gas in the diesel vehicle.

BACKGROUND OF THE INVENTION

Some diesel vehicles include a selective reduction catalyst for purifying nitrogen oxides contained in exhaust gas. The selective reduction catalyst reduces nitrogen oxides by using, as a reducer, ammonia gas produced from urea injected into the exhaust gas. In the case of a diesel vehicle including a selective reduction catalyst, it is desired to detect ammonia gas leaked into exhaust gas so as to appropriately control the injection amount of urea. In view of this, some diesel vehicles including such a selective reduction catalyst include a sensor which is sensitive to ammonia gas. The ammonia gas sensor disclosed in Japanese Unexamined Publication No. 2011-47758 can be used for such a purpose.

Problems to be Solved by the Invention

Incidentally, some diesel vehicles include not only a selective reduction catalyst but also an oxidation catalyst capable of oxidizing flammable gas contained in exhaust gas for purification of the flammable gas. In the case of a diesel vehicle including an oxidation catalyst, when the oxidation catalyst deteriorates, the amount of the flammable gas contained in the exhaust gas increases. In view of this, in the case of a diesel vehicle including an oxidation catalyst, it is desired to detect flammable gas contained in exhaust gas so as to determine whether or not the oxidation catalyst has deteriorated. Namely, in the case of a diesel vehicle including both a selective reduction catalyst and an oxidation catalyst, it is desired to detect ammonia gas and detect flammable gas. However, mounting a flammable gas detection sensor on a vehicle in addition to an ammonia gas detection sensor results in an increase in cost of the vehicle.

The present invention has been accomplished in view of the above problem, and its object is to provide a control apparatus and a gas detection method which can detect the concentration of ammonia gas and can determine whether or not an oxidation catalyst has deteriorated, while suppressing an increase in cost of a vehicle.

SUMMARY OF THE INVENTION

Means for Solving the Problems

A control apparatus according of one aspect of the present invention is mounted on a diesel vehicle which includes an oxidation catalyst provided in an exhaust gas passage of an engine and oxidizing flammable gas contained in exhaust gas, a selective reduction catalyst provided in the exhaust gas passage and reducing nitrogen oxides contained in the exhaust gas by using ammonia gas, and a gas sensor disposed in the exhaust gas passage to be located downstream of the oxidation catalyst and the selective reduction catalyst and configured to be sensitive to both the ammonia gas and the flammable gas. The control apparatus comprises an activation determination section, a concentration computation section, and a deterioration determination section.

The activation determination section determines whether or not the oxidation catalyst is in an activated state. The concentration computation section computes the concentration of the flammable gas from a sensor output of the gas sensor, while presuming that the sensor output corresponds to the concentration of the flammable gas, in an unactivated period during which the activation determination section determines that the oxidation catalyst is not in the activated state. The concentration computation section computes the concentration of the ammonia gas from the sensor output of the gas sensor, while presuming that the sensor output corresponds to the concentration of the ammonia gas, in an activated period during which the activation determination section determines that the oxidation catalyst is in the activated state. The deterioration determination section determines whether or not the oxidation catalyst has deteriorated in the unactivated period, based on the concentration of the flammable gas computed by the concentration computation section.

In such a diesel vehicle, in the unactivated period, the flammable gas is not oxidized, and therefore, the flammable gas remains in the exhaust gas. In the activated period subsequent to the unactivated period, the flammable gas is oxidized, and the amount of the flammable gas in the exhaust gas decreases. Also, in such a diesel vehicle, in the unactivated period, the injection of urea has not yet been started, and therefore, leakage of ammonia into the exhaust gas does not occur. In the activated period subsequent to the unactivated period, the injection of urea is started, and therefore, leakage of ammonia into the exhaust gas may occur. In view of this, in the unactivated period during which leakage of ammonia into the exhaust gas does not occur, the control apparatus computes the concentration of the flammable gas from the sensor output, while presuming that the sensor output corresponds to the concentration of the flammable gas, and determines whether or not the oxidation catalyst has deteriorated, on the basis of the computed concentration of the flammable gas. Also, in the activated period during which leakage of ammonia into the exhaust gas may occur, the control apparatus computes the concentration of the ammonia gas from the sensor output, while presuming that the sensor output corresponds to the concentration of the ammonia gas. Accordingly, by using the sensor output differently depending on the state of the vehicle, the control apparatus can detect the concentration of the ammonia gas and can determine whether or not the oxidation catalyst has deteriorated, while suppressing an increase in the cost of the vehicle.

In the above-described control apparatus, the concentration computation section may be configured to convert the sensor output to the concentration of the ammonia gas by using a first conversion parameter in the activated period, and convert the sensor output to the concentration of the flammable gas by using a second conversion parameter different from the first conversion parameter in the unactivated period.

The conversion parameter used for converting the sensor output to concentration is changed between when the ammonia gas concentration is computed and when the flammable gas concentration is computed. Therefore, even when the gas sensor has different sensitivities to the ammonia gas and the flammable gas, the ammonia gas concentration can be computed from the sensor output at the time of computation of the ammonia gas concentration, and the flammable gas concentration can be computed from the sensor output at the time of computation of the flammable gas concentration.

The control apparatus may comprise a heater control section configured to render a temperature of a heater in the unactivated period higher than a temperature of the heater in the activated period. The gas sensor may include a sensor element and the heater for heating the sensor element.

When the flammable gas concentration is computed, the temperature of the heater is rendered higher than that when the ammonia gas concentration is computed, whereby the sensitivity of the gas sensor to the flammable gas is increased. As a result, it is possible to adjust the sensitivity of the gas sensor to the ammonia gas at the time of computation of the ammonia gas concentration and the sensitivity of the gas sensor to the flammable gas at the time of computation of the flammable gas concentration such that the sensitivity to the ammonia gas becomes approximately the same as the sensitivity to the flammable gas.

In the above-described control apparatus, the concentration computation section may be configured to compute a conversion value by converting the sensor output by using a conversion parameter, use the conversion value as the concentration of the ammonia gas in the activated period, and compute the concentration of the flammable gas by multiplying the conversion value by a conversion coefficient in the unactivated period.

The sensor output is converted to a conversion value by using the same conversion parameter at the time of computation of the ammonia gas concentration and at the time of computation of the flammable gas concentration. At the time of computation of the ammonia gas concentration, the conversion value is used as the ammonia gas concentration as is. At the time of computation of the flammable gas concentration, a value obtained by multiplying the conversion value by the conversion coefficient is used as the flammable gas concentration. Therefore, even in the case where the gas sensor has different sensitivities to the ammonia gas and the flammable gas and the sensor output is converted by using the same conversion parameter, the ammonia gas concentration and the flammable gas concentration can be computed.

A gas detection method according to another aspect of the present invention is a method for detecting gases in a diesel vehicle which includes an oxidation catalyst provided in an exhaust gas passage of an engine and oxidizing flammable gas contained in exhaust gas, a selective reduction catalyst provided in the exhaust gas passage and reducing nitrogen oxides contained in the exhaust gas by using ammonia gas, and a gas sensor disposed in the exhaust gas passage to be located downstream of the oxidation catalyst and the selective reduction catalyst and configured to be sensitive to both the ammonia gas and the flammable gas. The gas detection method comprises an activation determination step, a concentration computation step, and a deterioration determination step.

The activation determination step determines whether or not the oxidation catalyst is in an activated state. The concentration computation step computes the concentration of the flammable gas from a sensor output of the gas sensor, while presuming that the sensor output corresponds to the concentration of the flammable gas, in an unactivated period during which the oxidation catalyst is determined in the activation determination step not to be in the activated state. The concentration computation step also computes the concentration of the ammonia gas from the sensor output of the gas sensor, while presuming that the sensor output corresponds to the concentration of the ammonia gas, in an activated period during which the oxidation catalyst is determined in the activation determination step to be in the activated state. The deterioration determination step determines whether or not the oxidation catalyst has deteriorated in the unactivated period, based on the concentration of the flammable gas computed in the concentration computation step.

According to this gas detection method, the same effect as the effect of the above-described control apparatus can be attained.

In the above-described gas detection method, the concentration computation step may include converting the sensor output to the concentration of the ammonia gas by using a first conversion parameter in the activated period, and converting the sensor output to the concentration of the flammable gas by using a second conversion parameter in the unactivated period.

According to this gas detection method, the same effect as the effect of the above-described control apparatus can be attained.

The gas sensor may include a sensor element and a heater for heating the sensor element, and the gas detection method may comprise a heater control step of controlling the heater such that a temperature of the heater in the unactivated period becomes higher than a temperature of the heater in the activated period.

According to this gas detection method, the same effect as the effect of the above-described control apparatus can be attained.

In the above-described gas detection method, the concentration computation step may include computing a conversion value by converting the sensor output by using a conversion parameter, using the conversion value as the concentration of the ammonia gas in the activated period, and computing the concentration of the flammable gas by multiplying the conversion value by a conversion coefficient in the unactivated period.

According to this gas detection method, the same effect as the effect of the above-described control apparatus can be attained.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Embodiments of the present invention will be described with reference to the drawings.

First Embodiment

<1. Engine Exhaust System>

A control apparatus of the present disclosure is an apparatus for detecting the concentrations of gases by using a gas sensor mounted on an engine exhaust system of a diesel vehicle.

Figure 1:
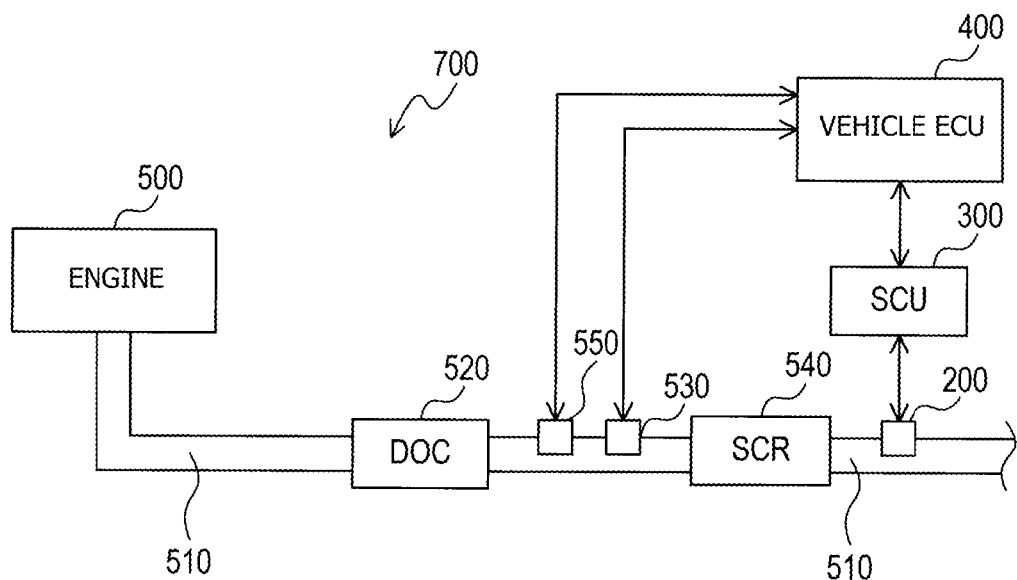
FIG. 1 is a block diagram showing the configuration of an engine exhaust system of an embodiment.

First, the configuration of the exhaust system of a diesel vehicle 700 will be briefly described with reference to FIG. 1. The exhaust system of the diesel vehicle 700 includes an engine 500, an exhaust pipe 510, a diesel oxidation catalyst 520, an injector 550, a selective reduction catalyst 540, a temperature sensor 530, a gas sensor 200, a sensor control unit 300, and a vehicle electronic control apparatus 400.

The engine 500 is a diesel engine. The exhaust pipe 510 is connected to exhaust ports of cylinders of the engine 500 and serves as an exhaust gas passage for discharging exhaust gas produced by the engine 500 to the outside.

The diesel oxidation catalyst 520 (hereinafter referred to as the "DOC 520") is provided in the exhaust pipe 510 and oxidizes flammable gas in the exhaust gas. Specifically, the DOC 520 oxidizes flammable harmful substances, such as carbon monoxide (CO) and hydrocarbon (HC), contained in the exhaust gas, thereby converting them to harmless substances such as water ($H_2O$) and carbon dioxide ($CO_2$). When the engine 500 starts its operation and the temperature of the DOC 520 becomes higher than a dew point (e.g., 100° C.), the DOC 520 becomes active and oxidizes the flammable gas. The dew point is the lowest temperature at which the DOC 520 becomes active.

The injector 550 is attached to the exhaust pipe 510 to be located on the downstream side of the DOC 520 and located on the upstream side of the selective reduction catalyst 540 (hereinafter referred to as the "SCR 540"). The injector 550 injects urea water stored in an unillustrated tank into the exhaust gas. The injector 550 injects the urea water in response to an injection instruction from the vehicle electronic control apparatus 400 (hereinafter referred to as the "vehicle ECU 400"). Namely, the injection amount of urea is controlled by the vehicle ECU 400.

The SCR 540 is a catalyst for reducing nitrogen oxides (NOx) contained in the exhaust gas by using ammonia ($NH_3$) gas, thereby converting NOx to harmless substances such as nitrogen ($N_2$) and $H_2O$. The ammonia gas is generated from the urea water injected by the injector 550. The injector 550 starts the injection of urea after the engine 500 has started its operation and the SCR 540 has become active as a result of an increase in the temperature of the SCR 540 (for example, to 150° C.). The timing at which the injector 550 injects urea is later than the timing at which the DOC 520 becomes active.

Notably, in the case where the engine 500 has an idle stop function, the injector 550 stops the injection of urea when the engine 500 is in an idle stop state. In the case where the idle stop period is short and a decrease in the temperature of the SCR 540 is small, the injector 550 resumes the injection of urea immediately after the restart of the engine 500. In this case, the temperature of the DOC 520 does not decrease to a temperature equal to or lower than the dew point, and the DOC 520 remains in the activated state. In the case where the idle stop period is long and a decrease in the temperature of the SCR 540 is large, the injector 550 resumes the injection of urea after the temperature of the SCR 540 increases again to the activation temperature.

The temperature sensor 530 is provided on the exhaust pipe 510 to be located on the downstream side of the DOC 520 and located on the upstream side of the SCR 540 and detects the temperature of the exhaust gas. The temperature sensor 530 transmits information of the detected temperature to the vehicle ECU 400.

The gas sensor 200 is provided on the exhaust pipe 510 to be located on the downstream side of the DOC 520 and the SCR 540 and is configured to be sensitive to both the ammonia gas and the flammable gas. The gas sensor 200 measures the concentrations of various types of gases to be measured which are contained in the exhaust gas, and transmits measurement signals to the sensor control unit 300 (hereinafter referred to as the "SCU 300"). The structure of the gas sensor 200 will be described in detail later.

The SCU 300 is mainly composed of a microcomputer including a CPU, a ROM, a RAM, etc. The SCU 300 is configured to enable two-way communications between the SCU 300 and the vehicle ECU 400. The SCU 300 executes a gas detection process. Specifically, the SCU 300 measures the the concentrations of the various types of gases to be measured by controlling the gas sensor 200, receives the various types of measurement signals from the gas sensor 200, computes the concentrations of the various types of gases to be measured, and determines whether or not the DOC 520 has deteriorated, on the bases of the computed concentration of the flammable gas. Also, the SCU 300 transmits various types of concentration signals and a deterioration presence/absence signal to the vehicle ECU 400. The gas detection process will be described in detail later.

The vehicle ECU 400 is mainly composed of a microcomputer including a CPU, a ROM, a RAM, etc., and executes various types of controls for the vehicle. As one of the various types of controls, the vehicle ECU 400 controls the amount of urea injected from the injector 550 on the basis of the ammonia gas concentration received from the SCU 300. Also, the vehicle ECU 400 detects deterioration of the DOC 520 upon receipt of a deterioration presence signal from the SCU 300.

<2. Gas Sensor>

Figure 2:
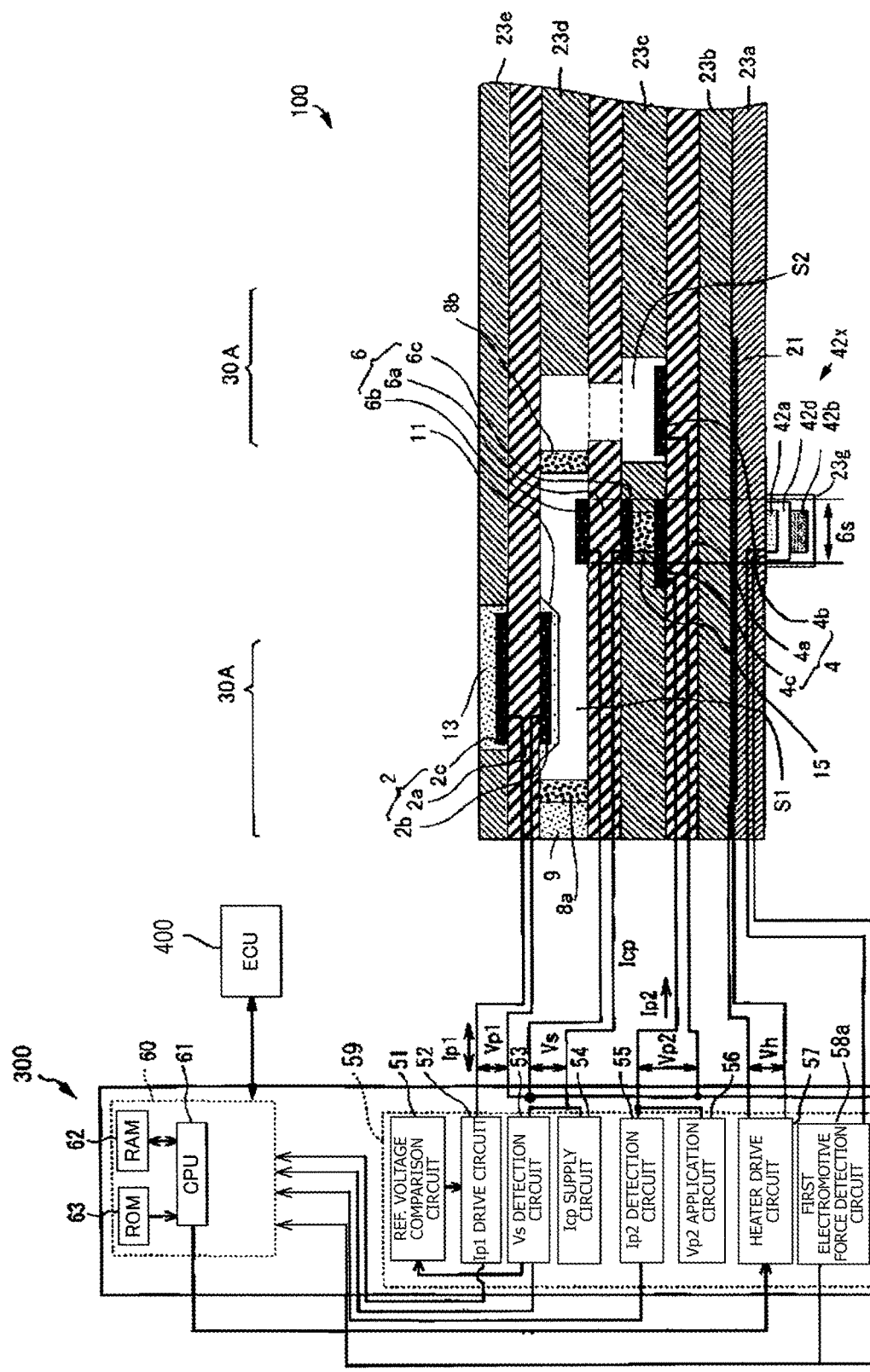
FIG. 2 is a diagram showing the structure of a gas sensor and the configuration of a sensor control apparatus.
Figure 3:
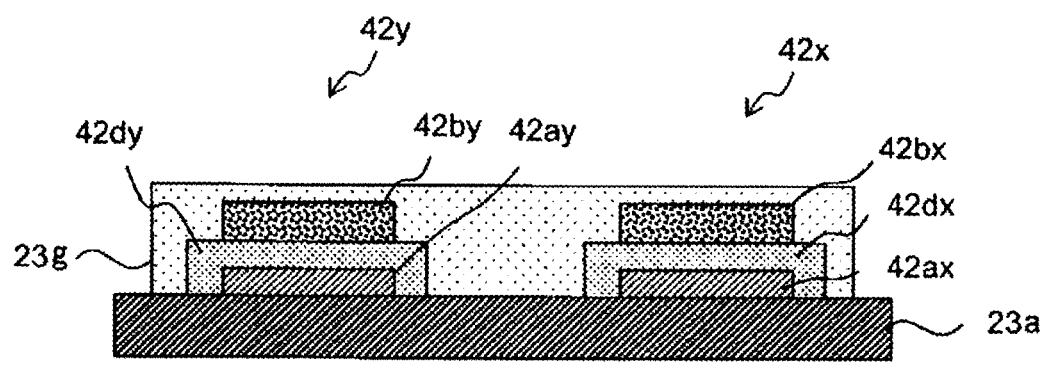
FIG. 3 is a view showing the structure of a first ammonia sensor section and a second ammonia sensor section.

Next, the structure of a sensor element section 100 of the gas sensor 200 will be described with reference to FIGS. 2 and 3. The gas sensor 200 includes the sensor element section 100 and an unillustrated housing. The sensor element section 100 is accommodated in the housing and is attached to the exhaust pipe 510 via the housing. The sensor element section 100 is a laminate elongated in an axial direction and includes an NOx sensor section 30A and two ammonia sensor sections; i.e., a first ammonia sensor section 42x and a second ammonia sensor section 42y. Notably, the left-hand side in FIG. 2 corresponds to a forward end side of the sensor element in the axial direction.

The NOx sensor section 30A has a structure in which an insulating layer 23e, a first solid electrolyte member 2a, an insulating layer 23d, a third solid electrolyte member 6a, an insulating layer 23c, a second solid electrolyte member 4a, and insulating layers 23b are 23a are stacked in this order. A first measurement chamber S1 is defined between the first solid electrolyte member 2a and the third solid electrolyte member 6a. A first diffusion resistor 8a is disposed at the left end (forward end side) of the first measurement chamber S1, and a protective layer 9 formed of a porous material is disposed on the outside of the first diffusion resistor 8a. The exhaust gas is externally introduced into the first measurement chamber S1 through the first diffusion resistor 8a.

A second diffusion resistor 8b is disposed at the right end (rear end) of the first measurement chamber S1, and a second measurement chamber S2 is defined on the right side (rear end side) of the second diffusion resistor 8b. The second measurement chamber S2 is an NOx measurement chamber where the concentration of NOx is measured. The second measurement chamber S2 is formed between the first solid electrolyte member 2a and the second solid electrolyte member 4a and penetrates through the third solid electrolyte member 6a.

A plate-shaped heat generation resistor 21 elongated in the longitudinal direction of the sensor element section 100 is disposed between the insulating layers 23b and 23a. The heat generation resistor 21 has a heat generation portion on a forward end side in the axial direction (longitudinal direction) and a pair of lead portions extending from the heat generation portion toward the rear end side in the axial direction. The heat generation resistor 21 and the insulating layers 23b and 23a correspond to the heater. This heater is used to heat the gas sensor to an activation temperature so as to increase the oxygen-ion conductivity of the solid electrolyte members, thereby stabilizing operation.

Each of the insulating layers 23a to 23e is formed mainly of alumina, and the first diffusion resistor 8a and the second diffusion resistor 8b are formed of a porous material such as alumina. The heat generation resistor 21 is formed of platinum or the like, and the heat generation portion of the heat generation resistor 21 is formed in, for example, a meandering pattern.

A first pumping cell 2 includes the first solid electrolyte member 2a formed mainly of zirconia having oxygen-ion conductivity and a pair of electrodes; i.e., an inside first pumping electrode 2b and an outside first pumping electrode 2c, which are formed mainly of platinum and are disposed to sandwich the first solid electrolyte member 2a. The inside first pumping electrode 2b faces the interior of the first measurement chamber S1. The surface of the inside first pumping electrode 2b is covered with a protective layer 11 formed of a porous material. A portion of the insulating layer 23e above the outside first pumping electrode 2c is removed to form an opening, and a porous member 13 fills the opening. This porous material 13 establishes communication between the outside first pumping electrode 2c and the outside space, thereby allowing a gas (specifically, oxygen) to flow between the outside first pumping electrode 2c and the outside space.

A oxygen concentration detection cell 6 includes the third solid electrolyte member 6a formed mainly of zirconia and a pair of electrodes; i.e., a detection electrode 6b and a reference electrode 6c, which are formed mainly of platinum and are disposed to sandwich the third solid electrolyte member 6a. The detection electrode 6b faces the interior of the first measurement chamber S1 at a position on the rear end side of the inside first pumping electrode 2b.

A portion of the insulating layer 23c is cut and removed to form a space in which the reference electrode 6c is disposed and into which a porous material is charged. The space serves as a reference oxygen chamber 15.

A second pumping cell 4 includes the second solid electrolyte member 4a formed mainly of zirconia and a pair of electrodes; i.e., an inside second pumping electrode 4b and a second pumping counterpart electrode 4c, which are formed mainly of platinum. The inside second pumping electrode 4b is disposed on a surface of the second solid electrolyte member 4a, which surface faces the interior of the second measurement chamber S2. The second pumping counterpart electrode 4c is disposed in a cutout space of the insulating layer 23c above the second solid electrolyte member 4a and faces the reference oxygen chamber 15 to be opposed to the reference electrode 6c. The inside first pumping electrode 2b, the detection electrode 6b, and the inside second pumping electrode 4b are connected to a reference potential line.

Next, the first ammonia sensor section 42x and the second ammonia sensor section 42y will be described. As shown in FIG. 3, the first ammonia sensor section 42x and the second ammonia sensor section 42y are formed on the insulating layer 23a such that the two ammonia sensor section 42x and 42y are spaced from each other in the width direction of the sensor element section 100. In FIG. 2, only the first ammonia sensor section 42x is illustrated.

The first ammonia sensor section 42x includes a first reference electrode 42ax formed on the insulating layer 23a, a first solid electrolyte member 42dx formed to cover the upper and side surfaces of the first reference electrode 42ax, and a first detection electrode 42bx formed on an upper surface of the first solid electrolyte member 42dx. The second ammonia sensor section 42y includes a second reference electrode 42ay, a second solid electrolyte member 42dy, and a second detection electrode 42by which are formed similarly.

The first ammonia sensor section 42x and the second ammonia sensor section 42y are sensitive to ammonia, flammable gas, and $NO_2$ and differ from each other in the ratio between the sensitivity to ammonia and flammable gas and the sensitivity to $NO_2$.

<3. Sensor Control Unit>

Next, an example of the configuration of the SCU 300 will be described. The SCU 300 includes a control circuit 59 and a microcomputer 60 provided on a circuit board. The microcomputer 60 includes a CPU 61, a RAM 62, a ROM 63, etc. The CPU 61 realizes various functions by executing a program stored in the ROM, etc.

The control circuit 59 includes a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57, and first and second electromotive force detection circuits 58a and 58b.

The heater drive circuit 57 is connected to the heat generation resistor 21 of the heater. When the heater drive circuit 57 receives electric power from an external power source as a result of the engine 500 being started, the heater drive circuit 57 activates the heater, thereby heating the first pumping cell 2, the oxygen concentration detection cell 6, and the second pumping cell 4 to the activation temperature. When the NOx sensor section 30A is heated to an appropriate temperature, the first ammonia sensor section 42x and the second ammonia sensor section 42y on the NOx sensor section 30A are also heated to a desired temperature.

The Ip1 drive circuit 52 is connected to the outside first pumping electrode 2c and supplies a first pumping current which flows between the inside first pumping electrode 2b and the outside first pumping electrode 2c. The first pumping cell 2 heated to the activation temperature pumps out oxygen contained in the exhaust gas having flowed into the first measurement chamber S1 so that oxygen flows from the inside first pumping electrode 2b toward the outside first pumping electrode 2c. At that time, the oxygen concentration within the first measurement chamber S1 corresponds to the inter-electrode voltage Vs of the oxygen concentration detection cell 6. The Ip1 drive circuit 52 controls the first pumping current Ip1 such that the voltage Vs becomes equal to a reference voltage Vbase (for example, 425 mV), thereby finely adjusting the oxygen concentration within the first measurement chamber S1 to a predetermined value at which decomposition of NOx does not occur. Further, the Ip1 drive circuit 52 detects the first pumping current Ip1 and outputs the detected first pumping current Ip1 to the microcomputer 60. The first pumping current Ip1 correlates with the oxygen concentration in the exhaust gas.

The Vs detection circuit 53 is connected to the reference electrode 6c. The Vs detection circuit 53 detects the voltage Vs between the detection electrode 6b and the reference electrode 6c and outputs the detected voltage Vs to the reference voltage comparison circuit 51 and the microcomputer 60. The reference voltage comparison circuit 51 compares the reference voltage Vbase and the voltage Vs and outputs the comparison result to the Ip1 drive circuit 52.

The Icp supply circuit 54 is connected to the reference electrode 6c and supplies a weak current Icp which flows between the detection electrode 6b and the reference electrode 6c so as to supply oxygen from the first measurement chamber S1 into the reference oxygen chamber 15, so that the reference electrode 6c is exposed to oxygen of a predetermined concentration (reference).

Vp2 application circuit 56 is connected to the second pumping counterpart electrode 4c. The exhaust gas whose oxygen concentration has been adjusted by the Ip1 drive circuit 52 further flows toward the second measurement chamber S2. The Vp2 application circuit 56 applies a predetermined voltage Vp2 (for example, 450 mV), at which decomposition of NOx gas in the exhaust gas to oxygen and nitrogen occurs, between the inside second pumping electrode 4b and the second pumping counterpart electrode 4c, thereby decomposing the NOx gas to oxygen and nitrogen.

The Ip2 detection circuit 55 is connected to the second pumping counterpart electrode 4c. A second pumping current Ip2 flows to the second pumping cell 4 so that oxygen produced as a result of decomposition of NOx is pumped out from the second measurement chamber S2. The Ip2 detection circuit 55 detects the second pumping current Ip2 flowing to the second pumping cell 4 when oxygen produced as a result of decomposition of NOx is pumped out from the second measurement chamber S2 to the second pumping counterpart electrode 4c side through the second solid electrolyte member 4a. The Ip2 detection circuit 55 outputs the detected second pumping current Ip2 to the microcomputer 60. This second pumping current Ip2 correlates with the NOx concentration in the exhaust gas.

The first electromotive force detection circuit 58a detects the electromotive force Vex between the pair of electrodes 42ax and 42bx of the first ammonia sensor section 42x and outputs the detected electromotive force Vex to the microcomputer 60. The second electromotive force detection circuit 58b detects the electromotive force Vey between the pair of electrodes 42ay and 42by of the second ammonia sensor section 42y and outputs the detected electromotive force Vey to the microcomputer 60. The electromotive force Vex between the pair of electrodes of the first ammonia sensor section 42x and the electromotive force Vey between the pair of electrodes of the second ammonia sensor section 42y correlate with the ammonia concentration.

The microcomputer 60 obtains the oxygen concentration by converting the first pumping current Ip1 to the oxygen concentration through use of a relational expression which represents the relation between the first pumping current Ip1 and the oxygen concentration. Also, the microcomputer 60 obtains the NOx concentration by converting the second pumping current Ip2 to the NOx concentration through use of a relational expression which represents the relation between the second pumping current Ip2 and the NOx concentration. The relational expression is determined in advance in accordance with the gas sensor 200 and is stored in the memory of the microcomputer 60.

Moreover, depending on the state of the exhaust system; specifically, the activation state of the DOC 520, the microcomputer 60 computes the ammonia gas concentration or the flammable gas concentration from the electromotive forces Vex and Vey of the first and second ammonia sensor sections 42x and 42y. In a period during which the DOC 520 is in the unactivated state (hereinafter referred to as the "unactivated period"), since the flammable gas is not oxidized, the flammable gas remains in the exhaust gas. In a period during which the DOC 520 is in the activated state (hereinafter referred to as the "activated period"), since the flammable gas is oxidized, the amount of the flammable gas in the exhaust gas decreases. Also, in the unactivated period during which the DOC 520 is in the unactivated state, the injection of urea by the injector 550 has not yet been started, leakage of ammonia gas into the exhaust gas does not occur. In contrast, in the activated period during which the DOC 520 is in the activated state, the injection of urea by the injector 550 is started, leakage of ammonia gas into the exhaust gas may occur.

In the unactivated period during which the DOC 520 is in the unactivated state, the microcomputer 60 regards the sensor outputs of the first and second ammonia sensor sections 42x and 42y as outputs corresponding to the flammable gas concentration, and computes the flammable gas concentration from the outputs. In the activated period during which the DOC 520 is in the activated state, the microcomputer 60 regards the sensor outputs of the first and second ammonia sensor sections 42x and 42y as outputs corresponding to the ammonia gas concentration, and computes the ammonia gas concentration from the outputs. Since the microcomputer 60 uses two sensor outputs which differ in sensitivity to $NO_2$ at the time of computation of the flammable gas concentration or the ammonia gas concentration, the microcomputer 60 can compute the flammable gas concentration or the ammonia gas concentration, while eliminating the influence of $NO_2$. In the following description, the first and second ammonia sensor sections 42x and 42y will be collectively referred to as the ammonia sensor section 42, and the electromotive forces Vex and Vey will be collectively referred to as the electromotive force Ve.

<4. Gas Detection Process>

Next, the steps of the gas detection process of a first embodiment will be described with reference to a flowchart of FIG. 4. The present gas detection process is one of control processes executed by the SCU 300. The SCU 300 starts the execution of the present gas detection process when the engine 500 starts its operation and continues the execution of the present gas detection process until the engine 500 stops its operation.

First, in S10, the SCU 300 starts heater control for the gas sensor 200.

Subsequently, in S20, the SCU 300 obtains, from the vehicle ECU 400, information of the temperature of the exhaust gas which is received from the temperature sensor 530 by the vehicle ECU 400. Notably, the SCU 300 may obtain the temperature information directly from the temperature sensor 530.

Subsequently, in S30, the SCU 300 determines whether the DOC 520 is in the activated state or in the unactivated state by using the temperature of the exhaust gas obtained in S20. Specifically, the SCU 300 compares the exhaust gas temperature with a temperature threshold. In the case where the exhaust gas temperature is equal to or lower than the temperature threshold, the SCU 300 determines that the DOC 520 is in the unactivated state and proceeds to S40. Meanwhile, in the case where the exhaust gas temperature is higher than the temperature threshold, the SCU 300 determines that the DOC 520 is in the activated state and proceeds to S80. The temperature threshold used here may be the above-described dew point.

In S40, the SCU 300 sets flammable gas parameters for converting the electromotive force Ve, which is the sensor output of the ammonia sensor section 42, to the flammable gas concentration. The flammable gas parameters are all the coefficients contained in various types of relational expressions representing the relation between the electromotive force Ve and the flammable gas concentration. The flammable gas parameters are determined in advance in accordance with the gas sensor 200 and are stored in the memory of the SCU 300.

Subsequently, in S50, the SCU 300 computes the flammable gas concentration from the electromotive force Ve by using the flammable gas parameters set in S40.

Subsequently, in S60, the SCU 300 determines whether or not the DOC 520 has deteriorated by using the flammable gas concentration computed in S50. Even in the unactivated period, if the DOC 520 has deteriorated, the flammable gas concentration in the exhaust gas becomes high as compared with the case where the DOC 520 has not yet deteriorated. Therefore, the flammable gas concentration can be used for determination as to whether or not the DOC 520 has deteriorated. Specifically, the SCU 300 compares the flammable gas concentration with a concentration threshold. In the case where the flammable gas concentration is equal to or higher than the concentration threshold, the SCU 300 determines that the DOC 520 has deteriorated and proceeds to S70. In S70, the SCU 300 detects the deterioration of the DOC 520, transmits the detection result to the vehicle ECU 400, and returns to S20.

Meanwhile, in the case where the flammable gas concentration is lower than the concentration threshold, the SCU 300 determines that the DOC 520 has not yet deteriorated and returns to S20. The SCU 300 repeatedly executes the processing of S20 to S70 during the unactivated period; i.e., until the SCU 300 determines in S30 that the DOC 520 is in the activated state.

Notably, once the SCU 300 detects the deterioration of the DOC 520, the SCU 300 does not clear the detection result until the engine 500 stops and starts again. Therefore, after the SCU 300 detects the deterioration of the DOC 520 one time, the SCU 300 may repeat only the processing of S20 and S30 during the unactivated period without performing the processing of S40 to S70.

Meanwhile, in the case where the SCU 300 determines in S30 that the DOC 520 is in the activated state, in S80, the SCU 300 sets ammonia gas parameters for converting the electromotive force Ve to the ammonia gas concentration. The ammonia gas concentration can be computed by a publicly known method described in Japanese Patent Application Laid-Open (kokai) No. 2015-34814 (particularly, paragraph 0057 to paragraph 0063). The ammonia gas parameters are all the coefficients contained in various types of relational expressions which represent the relation between the electromotive force Ve and the ammonia gas concentration and are used in the publicly known method or the like. The ammonia gas parameters, which differ from the flammable gas parameters, are determined in advance in accordance with the gas sensor 200 and are stored in the memory of the SCU 300.

The reason why the conversion parameters used for computation of the flammable gas concentration from the electromotive force Ve differ from those used for computation of the ammonia gas concentration from the electromotive force Ve is that the sensitivity of the ammonia sensor section 42 to the ammonia gas differs from the sensitivity of the ammonia sensor section 42 to the flammable gas.

Subsequently, in S90, the SCU 300 computes the ammonia gas concentration from the electromotive force Ve by using the ammonia gas parameters set in S80 and transmits the computed ammonia gas concentration to the vehicle ECU 400. After that, the SCU 300 returns to S80 and repeats the processing of S80 and S90 until the engine 500 stops. Namely, after the SCU 300 determines once that the DOC 520 is in the activated state, the activated period continues until the engine 500 stops. When the engine 500 stops, the present process ends.

<5. Effects>

According to the first embodiment having been described above, the following effects are obtained.

(1) In the unactivated period during which leakage of ammonia gas to the exhaust gas does not occur, the SCU 300 presumes that the sensor output corresponds to the flammable gas concentration, computes the flammable gas concentration from the sensor output, and determines whether or not the DOC 520 has deteriorated, on the basis of the computed flammable gas concentration. In the activated period during which leakage of ammonia gas to the exhaust gas may occur, the SCU 300 presumes that the sensor output corresponds to the ammonia gas concentration, and computes the ammonia gas concentration from the sensor output. Accordingly, by using the sensor output differently depending on the state of the diesel vehicle 700, the SCU 300 can detect the ammonia gas concentration and can determine whether or not the DOC 520 has deteriorated, while suppressing the cost of the diesel vehicle 700.

(2) The conversion parameters used for converting the sensor output to concentration are changed between when the ammonia gas concentration is computed and when the flammable gas concentration is computed. Therefore, even when the gas sensor 200 has different sensitivities to ammonia gas and flammable gas, the ammonia gas concentration and the flammable gas concentration can be computed from the sensor output.

<6. Experiment>

Figure 5:
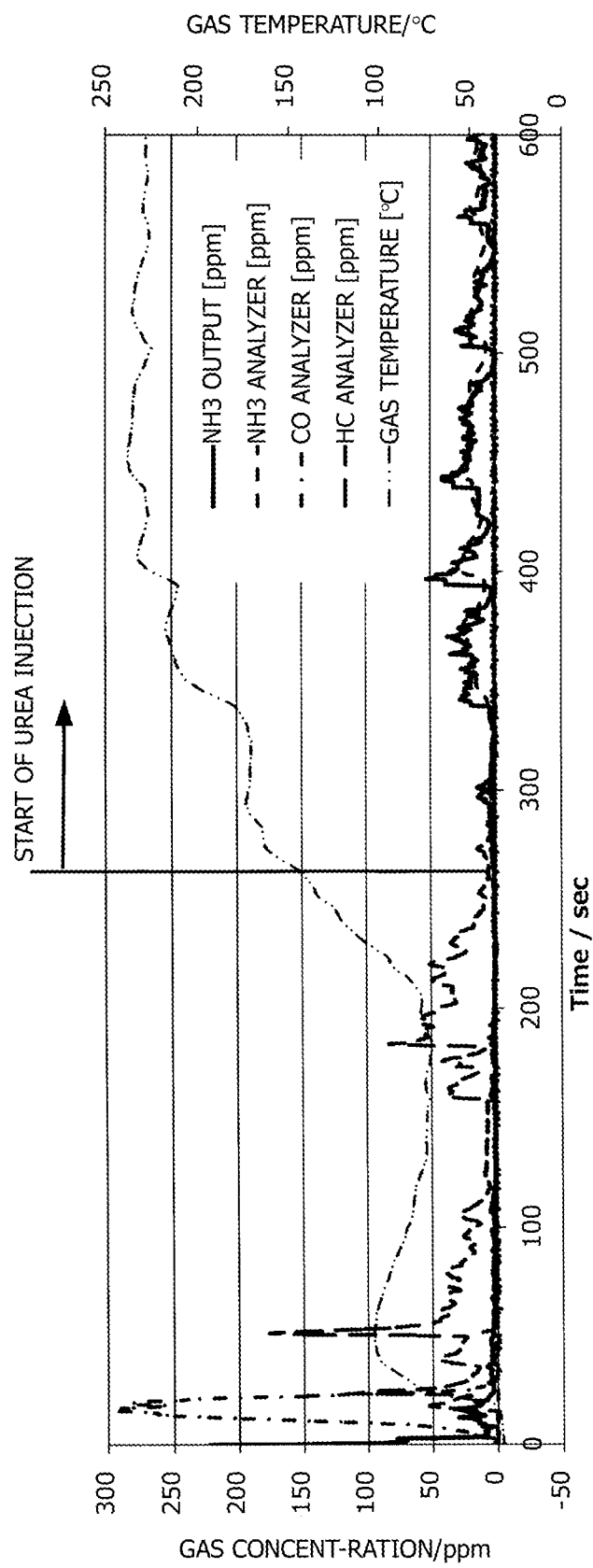
FIG. 5 is a time chart of the concentration of gas computed from an output of the gas sensor for the case where conversion parameters are maintained constant, the concentrations of $NH_3$, CO, and HC detected through use of analyzers, and gas temperature.
Figure 6:
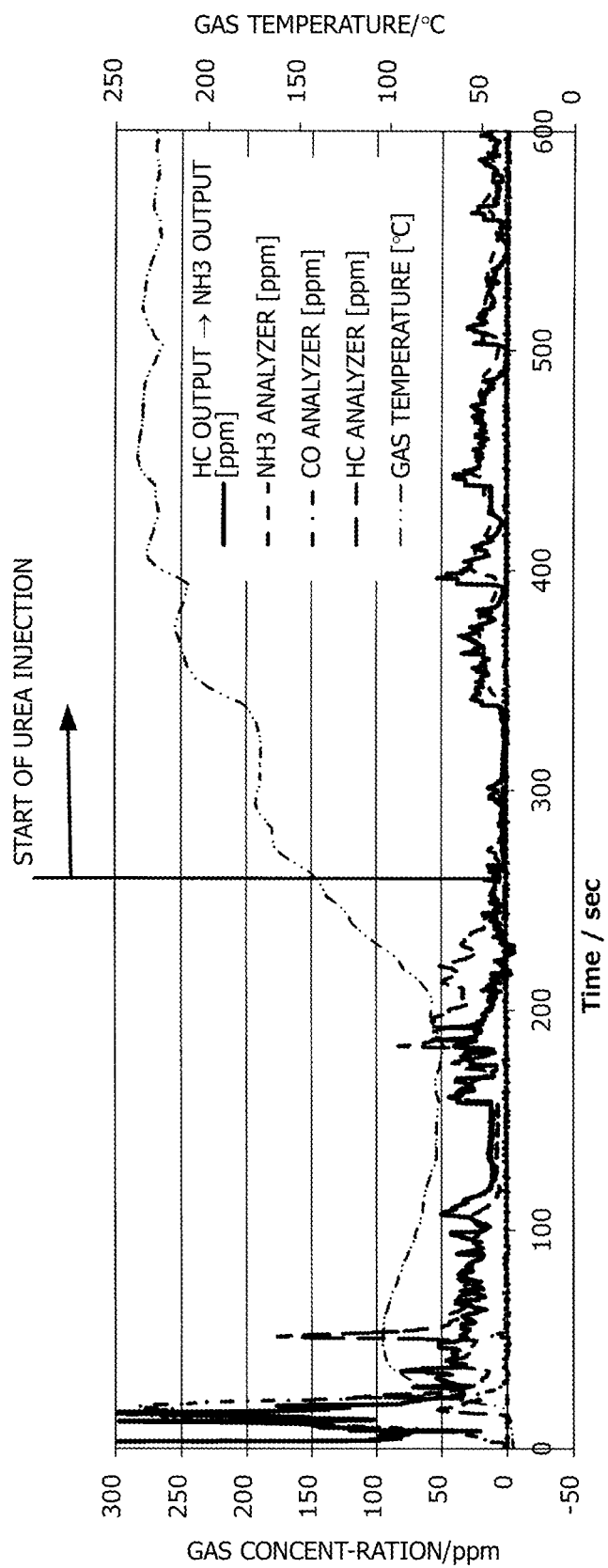
FIG. 6 is a time chart of the concentration of gas computed from an output of the gas sensor for the case where the conversion parameters are changed depending on whether or not an oxidation catalyst is in an activated state, the concentrations of $NH_3$, CO, and HC detected through use of analyzers, and gas temperature.

FIG. 5 shows the time chart of the gas concentration computed from the sensor output for the case where the sensor output is presumed to correspond to the ammonia gas concentration and only the ammonia gas parameters are used as conversion parameters. FIG. 5 also shows the time chart of various types of gas concentrations detected by various types of analyzers. FIG. 6 shows the time chart of the gas concentration computed from the sensor output for the case where, depending on the result of the determination as to whether the exhaust gas temperature is equal to or lower than the temperature threshold, the sensor output is presumed to correspond to the flammable gas concentration or the ammonia gas concentration and the flammable gas parameters or the ammonia gas parameters are used as conversion parameters. FIG. 6 also shows the time chart of various types of gas concentrations detected by various types of analyzers.

In FIG. 5, in the unactivated period during which the DOC 520 is in the unactivated state, whereas the concentrations of flammable gases (CO, HC) detected by analyzers are relatively high, the gas concentration computed from the sensor output is relatively low. This is because the ammonia gas parameters are used as conversion parameters, and therefore, the computed concentration of flammable gas to which the gas sensor has a lower sensitivity than that to ammonia gas is lower than the actual concentration. In FIG. 5, after the injection of urea is started, the gas concentration computed from the sensor output is approximately the same as the ammonia gas concentration detected by the analyzer.

Meanwhile, in FIG. 6, in the unactivated period during which the DOC 520 is in the unactivated state, the gas concentration computed from the sensor output is approximately the same as the sum of the CO gas concentration and the HC gas concentration detected by the analyzers. In FIG. 6 as well, after the injection of urea is started, the gas concentration computed from the sensor output is approximately the same as the ammonia gas concentration detected by the analyzer.

<7. Correspondence of Terms>

In the present embodiment, the SCU 300 corresponds to the control apparatus in the claims, and the exhaust pipe 510 corresponds to the exhaust gas passage in the claims. The sensor element section 100 corresponds to the sensor element in the claims, and the microcomputer 60 and the heater drive circuit 57 correspond to the heater control section in the claims. The processing of S30 corresponds to the function of the activation determination section in the claims, and the processing of S40, S50, S80, and S90 corresponds to the function of the concentration computation section in the claims. The processing of S60 and S70 corresponds to the function of the deterioration determination section in the claims.

Second Embodiment

<1. Difference from First Embodiment>

Since the basic configuration of the second embodiment is the same as that of the first embodiment, the configuration common between the first and second embodiments will not be described, and the different point will be mainly described. Notably, the same symbols as those in the first embodiment denote the same elements, and the preceding description therefor will be referred to.

In the above-described first embodiment, the conversion parameters are changed between the unactivated period during which the DOC 520 is in the unactivated state and the activated period during which the DOC 520 is in the activated state, whereby the flammable gas concentration is computed from the sensor output in the unactivated period, and the ammonia gas concentration is computed from the sensor output in the activated period. The second embodiment differs from the first embodiment in the point that only the ammonia gas parameters are used as the conversion parameters in both the unactivated period and the activated period and the temperature of the heater of the gas sensor 200 is changed between the unactivated period and the activated period.

Figure 7:
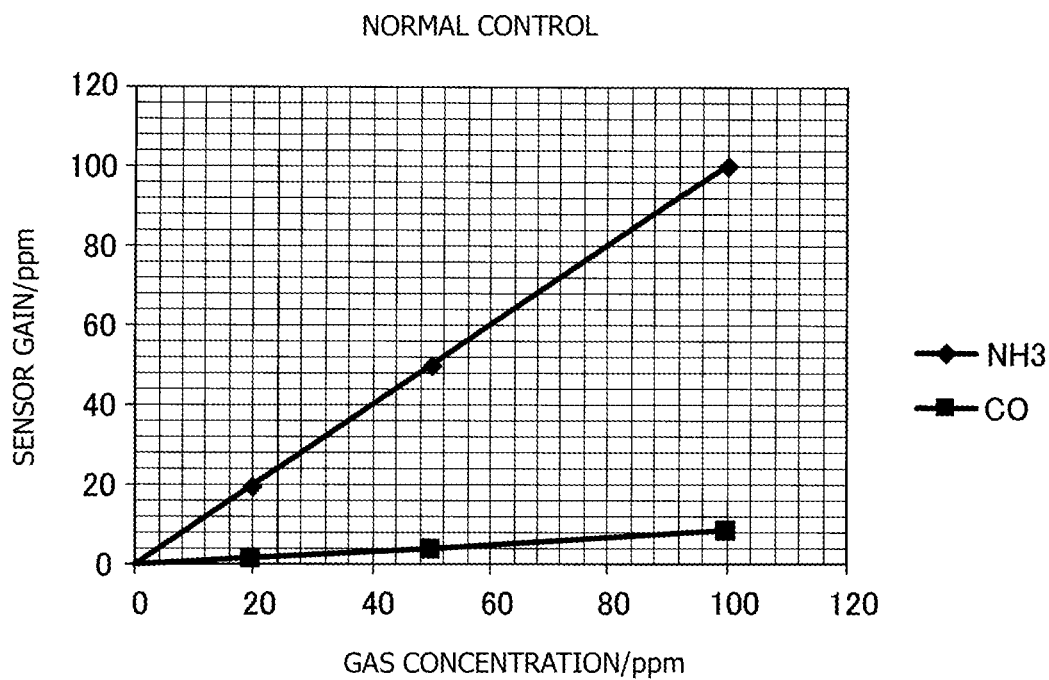
FIG. 7 is a graph showing the gain of the gas sensor for gas concentration in the case where the temperature of a heater is controlled to by normal control.
Figure 8:
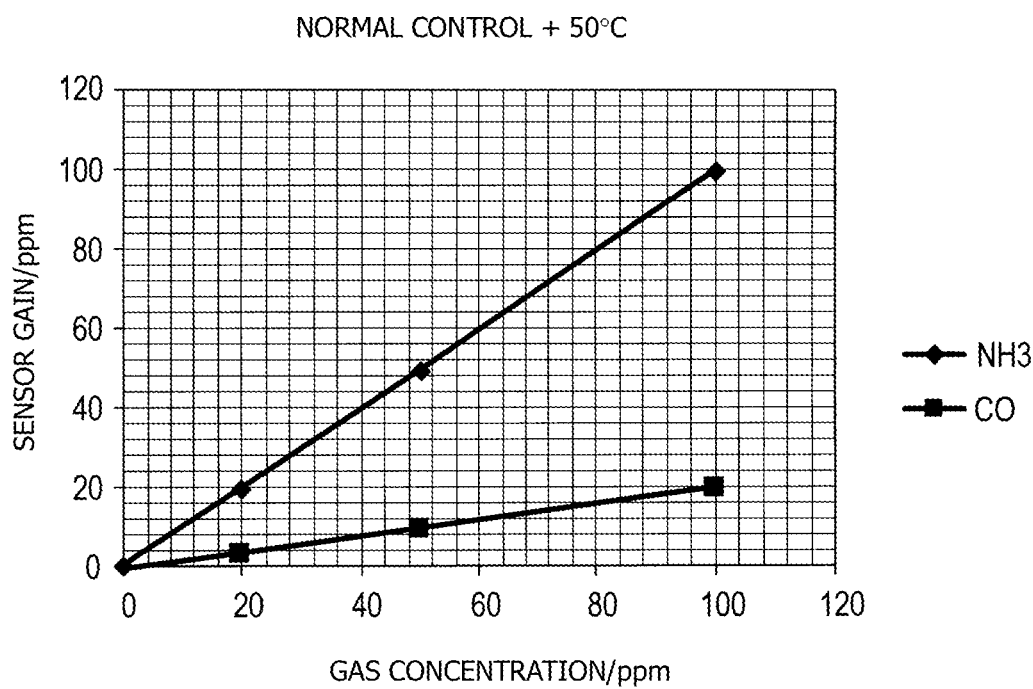
FIG. 8 is a graph showing the gain of the gas sensor for gas concentration in the case where the temperature of the heater is controlled to a temperature higher than that in the normal control.

FIG. 7 shows the sensor gain of the gas sensor 200 for the gas concentrations of ammonia gas and CO for the case where the temperature of the heater is controlled by normal control. FIG. 8 shows the sensor gain of the gas sensor 200 for the gas concentrations of ammonia gas and CO for the case where the temperature of the heater is controlled such that the temperature of the heater becomes 50° C. higher than that in the normal control. Notably, in the first embodiment, the temperature of the heater of the gas sensor 200 is controlled by normal control.

Comparison of FIGS. 7 and 8 reveals that, whereas the gain for the ammonia gas concentration does not change even when the temperature of the heater is increased, the gain for the CO gas concentration increases when the temperature of the heater is increased. Namely, when the temperature of the heater is increased, the sensitivity of the gas sensor 200 to the flammable gas increases.

Figure 4:
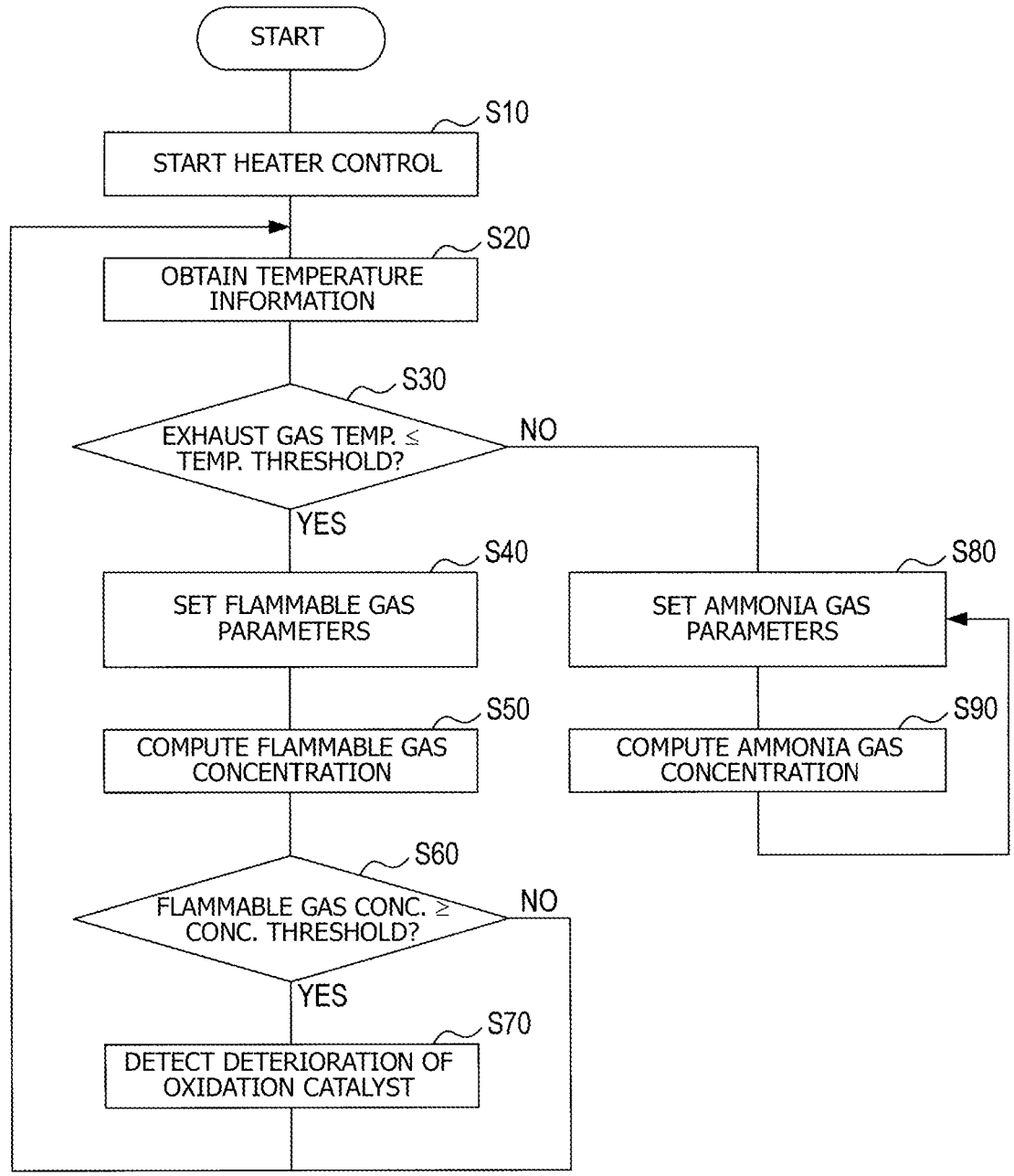
FIG. 4 is a flowchart showing the steps of a process of detecting gas concentration.

In view of this, in the second embodiment, in S40 of the flowchart of FIG. 4, the SCU 300 sets the temperature of the heater to a temperature higher than that in the normal control, instead of setting the flammable gas parameters. Also, in S80, the SCU 300 sets the temperature of the heater to the temperature in the normal control instead of setting the ammonia gas parameters.

Notably, the processing of changing the conversion parameters may be combined with the processing of changing the temperature of the heater. Namely, the process shown by the flowchart of FIG. 4 may be modified as follows. In S40, the SCU 30 sets the flammable gas parameters and sets the temperature of the heater to a temperature higher than that in the normal control. In S80, the SCU 30 sets the ammonia gas parameters and sets the temperature of the heater to the temperature in the normal control. In this case, the flammable gas parameters and the ammonia gas parameters and the temperature of the heater are set to values different from those in the case where only one of the processing of changing the conversion parameters and the processing of changing the temperature of the heater is performed.

<2. Effects>

According to the second embodiment having been described above, the following effect is obtained in addition to the above-described effect (1) of the first embodiment.

(3) When the flammable gas concentration is computed, the temperature of the heater is rendered higher than that when the ammonia gas concentration is computed, whereby the sensitivity of the gas sensor 200 to the flammable gas is increased. As a result, it is possible to adjust the sensitivity of the gas sensor 200 to the ammonia gas at the time of computation of the ammonia gas concentration and the sensitivity of the gas sensor 200 to the flammable gas at the time of computation of the flammable gas concentration such that the sensitivity to the ammonia gas becomes approximately the same as the sensitivity to the flammable gas.

Third Embodiment

<1. Difference from First Embodiment>

Since the basic configuration of the third embodiment is the same as that of the first embodiment, the configuration common between the first and third embodiments will not be described, and the different point will be mainly described.

Notably, the same symbols as those in the first embodiment denote the same elements, and the preceding description therefor will be referred to.

In the above-described first embodiment, the conversion parameters are changed between the unactivated period during which the DOC 520 is in the unactivated state and the activated period during which the DOC 520 is in the activated state, whereby the flammable gas concentration is computed from the sensor output in the unactivated period, and the ammonia gas concentration is computed from the sensor output in the activated period. The third embodiment differs from the first embodiment in the point that a conversion value is computed by using only the ammonia gas parameters as the conversion parameters in both the unactivated period and the activated period; in the unactivated period, the flammable gas concentration is computed by multiplying the computed conversion value by a conversion coefficient; and in the activated period, the computed conversion value is used as the ammonia gas concentration.

Namely, in the first embodiment, the difference between the sensitivity of the ammonia sensor section 42 to the flammable gas and the sensitivity of the ammonia sensor section 42 to the ammonia gas is corrected through use of the conversion parameters. In contrast, in the third embodiment, the difference in sensitivity is corrected through use of a conversion coefficient.

In the third embodiment, the SCU 30 computes the conversion value from the sensor output through use of the ammonia gas parameters between S10 and S20 of the flowchart of FIG. 4. The SCU 30 proceeds to S50, without executing the processing of S40, so as to compute the flammable gas concentration by multiplying the computed conversion value by the conversion coefficient. The SCU 30 proceeds to S90, without executing the processing of S80, so as to use the computed conversion value as the ammonia gas concentration.

<2. Effects>

According to the third embodiment having been described above, the following effect is obtained in addition to the above-described effect (1) of the first embodiment.

(4) The sensor output is converted to a conversion value by using the same conversion parameters at the time of computation of the ammonia gas concentration and at the time of computation of the flammable gas concentration. At the time of computation of the ammonia gas concentration, the conversion value is used as the ammonia gas concentration as is. At the time of computation of the flammable gas concentration, a value obtained by multiplying the conversion value by the conversion coefficient is used as the flammable gas concentration. Therefore, even in the case where the gas sensor 200 has different sensitivities to the ammonia gas and the flammable gas and the sensor output is converted by using the same conversion parameters, the ammonia gas concentration and the flammable gas concentration can be computed.

Other Embodiments

While embodiments of the present disclosure have been described, the present disclosure is not limited to the embodiments. The present disclosure can be implemented in various forms.

(a) In the above-described embodiments, the SCU 300 corresponds to the control apparatus. However, this is not a limitation. The control apparatus may be composed of the SCU 300 and the vehicle ECU 400. Namely, the embodiments may be modified such that the SCU 300 executes a portion of the gas detection process and the vehicle ECU 400 executes the remaining portion.

For example, in the case of the first embodiment, the SCU 300 may transmit the sensor output to the vehicle ECU 400. In this case, the vehicle ECU 400 may determine whether or not the DOC 520 is in the activated state, compute the flammable gas concentration or the ammonia gas concentration from the sensor output by using the flammable gas parameters or the ammonia gas parameters depending on the result of the determination, and determine whether or not the DOC 520 has deteriorated.

Also, in the case of the third embodiment, the SCU 300 may transmit the computed conversion value to the vehicle ECU 400. In this case, the vehicle ECU 400 may determine whether or not the DOC 520 is in the activated state. In the case where the DOC 520 is in the unactivated state, the vehicle ECU 400 may compute the flammable gas concentration by multiplying the conversion value by the conversion coefficient and determine whether or not the DOC 520 has deteriorated. Further, in the case where the DOC 520 is in the activated state, the vehicle ECU 400 may use the conversion value as the ammonia gas concentration.

Alternatively, in each embodiment, the SCU 300 may transmit the computed flammable gas concentration and the computed ammonia gas concentration to the vehicle ECU 400, and the vehicle ECU 400 may determine whether or not the DOC 520 has deteriorated, on the basis of the received flammable gas concentration.

(b) The gas sensor 200 is a multi sensor including the first and second ammonia sensor sections 42x and 42y and the NOx sensor section 30A. However, the gas sensor 200 is not required to be a multi sensor and may be a sensor including at least one ammonia sensor section.

(c) In the above-described embodiments, the temperature of exhaust gas is used as the temperature of the DOC 520. However, in the case where the temperature of the DOC 520 can be measured directly, the temperature of the DOC 520 may be used.

(d) A plurality of functions of a single constituent element in the above embodiments may be realized by a plurality of constituent elements, and a single function of a single constituent element may be realized by a plurality of constituent elements. Also, a plurality of functions of a plurality of constituent elements may be realized by a single constituent element, and a single function realized by a plurality of constituent elements may be realized by a single constituent element. Also, the configurations of the above embodiments may be partially eliminated. Also, at least a portion of the configuration of one of the above embodiments may be added to the configuration of another embodiment or replace a portion of the configuration of another embodiment. All modes contained in the technical idea specified only by the wording of the appended claims are embodiments of the present disclosure.

(e) The present disclosure may be realized in various forms other than the above-described control apparatus and gas detection method. The present disclosure may be implemented as a system including the control apparatus as a constituent element, a program that realizes the gas detection method by a computer, and a non-transitory tangible recording medium, e.g., a semiconductor memory, in which the program is stored.

DESCRIPTION OF REFERENCE NUMERALS AND SYMBOLS

2 . . . first pumping cell; 2a . . . first solid electrolyte member; 2b . . . inside first pumping electrode; 2c . . . outside first pumping electrode; 4 . . . second pumping cell; 4a . . . second solid electrolyte member; 4b . . . inside second pumping electrode; 4c . . . second pumping counterpart electrode; 6 . . . oxygen concentration detection cell; 6a . . . third solid electrolyte member; 6b . . . detection electrode; 6c . . . reference electrode; 8a . . . first diffusion resistor; 8b . . . second diffusion resistor; 9, 11 . . . protective layer; 13 . . . porous material; 15 . . . reference oxygen chamber; 21 . . . heat generation resistor; 23a to 23e . . . insulating layer; 30A . . . NOx sensor section; 42x . . . first ammonia sensor section; 42y . . . second ammonia sensor section; 42ax . . . first reference electrode; 42ay . . . second reference electrode; 42bx . . . first detection electrode; 42by . . . second detection electrode; 42dx . . . first solid electrolyte member; 42dy . . . second solid electrolyte member; 51 . . . reference voltage comparison circuit; 52 . . . Ip1 drive circuit; 53 . . . Vs detection circuit; 54 . . . Icp supply circuit; 55 . . . Ip2 detection circuit; 56 . . . Vp2 application circuit; 57 . . . heater drive circuit; 58a . . . first electromotive force detection circuit; 58b . . . second electromotive force detection circuit; 59 . . . control circuit; 60 . . . microcomputer; 61 . . . CPU; 62 . . . RAM; 63 . . . ROM; 100 . . . sensor element section; 200 . . . gas sensor; 300 . . . SCU; 400 . . . vehicle ECU; 500 . . . engine; 510 . . . exhaust pipe; 520 . . . DOC; 530 . . . temperature sensor; 540 . . . SCR; 550 . . . injector.

The invention claimed is:

1. A control apparatus mounted on a diesel vehicle which includes an oxidation catalyst provided in an exhaust gas passage of an engine and oxidizing flammable gas contained in exhaust gas, a selective reduction catalyst provided in the exhaust gas passage and reducing nitrogen oxides contained in the exhaust gas by using ammonia gas, and a gas sensor disposed in the exhaust gas passage to be located downstream of the oxidation catalyst and the selective reduction catalyst and configured to be sensitive to both the ammonia gas and the flammable gas, the control apparatus comprising:
an activation determination section configured to determine whether or not the oxidation catalyst is in an activated state;
a concentration computation section configured to compute a concentration of the flammable gas from a sensor output of the gas sensor, while presuming that the sensor output corresponds to the concentration of the flammable gas, in an unactivated period during which the activation determination section determines that the oxidation catalyst is not in the activated state and to compute a concentration of the ammonia gas from the sensor output of the gas sensor, while presuming that the sensor output corresponds to the concentration of the ammonia gas, in an activated period during which the activation determination section determines that the oxidation catalyst is in the activated state; and
a deterioration determination section configured to determine whether or not the oxidation catalyst has deteriorated in the unactivated period, based on the concentration of the flammable gas computed by the concentration computation section.

2. The control apparatus according to claim 1, wherein the concentration computation section is configured to convert the sensor output to the concentration of the ammonia gas by using a first conversion parameter in the activated period and convert the sensor output to the concentration of the flammable gas by using a second conversion parameter different from the first conversion parameter in the unactivated period.

3. The control apparatus according to claim 1, further comprising a heater control section configured to render a temperature of a heater in the unactivated period higher than a temperature of the heater in the activated period, wherein
the gas sensor includes a sensor element and the heater for heating the sensor element.

4. The control apparatus according to claim 1, wherein the concentration computation section is configured to compute a conversion value by converting the sensor output by using a conversion parameter, use the conversion value as the concentration of the ammonia gas in the activated period, and compute the concentration of the flammable gas by multiplying the conversion value by a conversion coefficient in the unactivated period.

5. A gas detection method for detecting gases in a diesel vehicle which includes an oxidation catalyst provided in an exhaust gas passage of an engine and oxidizing flammable gas contained in exhaust gas, a selective reduction catalyst provided in the exhaust gas passage and reducing nitrogen oxides contained in the exhaust gas by using ammonia gas, and a gas sensor disposed in the exhaust gas passage to be located downstream of the oxidation catalyst and the selective reduction catalyst and configured to be sensitive to both the ammonia gas and the flammable gas, the gas detection method comprising:
an activation determination step of determining whether or not the oxidation catalyst is in an activated state;
a concentration computation step of computing a concentration of the flammable gas from a sensor output of the gas sensor, while presuming that the sensor output corresponds to the concentration of the flammable gas, in an unactivated period during which the oxidation catalyst is determined in the activation determination step not to be in the activated state and computing a concentration of the ammonia gas from the sensor output of the gas sensor, while presuming that the sensor output corresponds to the concentration of the ammonia gas, in an activated period during which the oxidation catalyst is determined in the activation determination step to be in the activated state; and
a deterioration determination step of determining whether or not the oxidation catalyst has deteriorated in the unactivated period, based on the concentration of the flammable gas computed in the concentration computation step.

6. The gas detection method according to claim 5, wherein the concentration computation step includes converting the sensor output to the concentration of the ammonia gas by using a first conversion parameter in the activated period, and converting the sensor output to the concentration of the flammable gas by using a second conversion parameter different from the first conversion parameter in the unactivated period.

7. The gas detection method according to claim 5, wherein
the gas sensor includes a sensor element and a heater for heating the sensor element; and
the gas detection method comprises a heater control step of controlling the heater such that a temperature of the heater in the unactivated period becomes higher than a temperature of the heater in the activated period.

8. The gas detection method according to claim 5, wherein the concentration computation step includes computing a conversion value by converting the sensor output by using a conversion parameter, using the conversion value as the concentration of the ammonia gas in the activated period, and computing the concentration of the flammable gas by multiplying the conversion value by a conversion coefficient in the unactivated period.

9. The control apparatus according to claim 1, wherein the control apparatus is configured to detect an electromotive force that is output from the gas sensor and regard the electromotive force as the sensor output.

10. The control apparatus according to claim 9, wherein the electromotive force correlates with the concentration of the ammonia gas.

11. The control apparatus according to claim 1, wherein the flammable gas comprises at least one of carbon monoxide and hydrocarbon.

\* \* \* \* \*